(12) United States Patent
Donskey et al.

(10) Patent No.: US 10,550,437 B2
(45) Date of Patent: Feb. 4, 2020

(54) *CLOSTRIDIUM DIFFICILE* CULTURE MEDIUM

(71) Applicant: CASE WESTERN RESERVE UNIVERSITY, Cleveland, OH (US)

(72) Inventors: Curtis Donskey, Cleveland, OH (US); Michelle Nerandzic, Cleveland, OH (US); Jennifer Cadnum, Cleveland, OH (US)

(73) Assignee: CASE WESTERN RESERVE UNIVERSITY, Cleveland, OH (US)

( * ) Notice: Subject to any disclaimer, the term of this patent is extended or adjusted under 35 U.S.C. 154(b) by 100 days.

(21) Appl. No.: 15/315,240

(22) PCT Filed: Jun. 1, 2015

(86) PCT No.: PCT/US2015/033592
§ 371 (c)(1),
(2) Date: Nov. 30, 2016

(87) PCT Pub. No.: WO2015/184454
PCT Pub. Date: Dec. 3, 2015

(65) Prior Publication Data
US 2017/0114395 A1   Apr. 27, 2017

Related U.S. Application Data

(60) Provisional application No. 62/005,120, filed on May 30, 2014.

(51) Int. Cl.
*C12Q 1/689* (2018.01)
*G01N 33/52* (2006.01)
*G01N 33/68* (2006.01)

(52) U.S. Cl.
CPC .......... *C12Q 1/689* (2013.01); *G01N 33/523* (2013.01); *G01N 33/6893* (2013.01); *C12Q 2600/158* (2013.01); *G01N 2333/902* (2013.01); *G01N 2800/26* (2013.01)

(58) Field of Classification Search
None
See application file for complete search history.

(56) References Cited

U.S. PATENT DOCUMENTS

| 2008/0199904 | A1 | 8/2008 | Suslick et al. |
| 2008/0261264 | A1 | 10/2008 | Araujo Prado et al. |
| 2011/0319340 | A1 | 12/2011 | Carney |
| 2012/0288508 | A1* | 11/2012 | Ambrosino ............ A61K 39/08 424/150.1 |

OTHER PUBLICATIONS

Nerandzic, et al. "Effective and Reduced-Cost Modified Selective Medium for Isolation of Clostridium Difficile", Journal of Clinical Microbiology, Feb. 2009, vol. 47, No. 2, p. 397-400.

* cited by examiner

*Primary Examiner* — Patricia Duffy
(74) *Attorney, Agent, or Firm* — Tarolli, Sundheim, Covell & Tummino LLP

(57) ABSTRACT

A culture medium for culturing *Clostridium difficile* under aerobic culture conditions, the medium includes a nutrient medium that promotes growth of *Clostridium difficile* and amounts of thioglycolic and L-cystine effective to consume oxygen in the culture medium and facilitate growth of *Clostridium difficile*.

1 Claim, 3 Drawing Sheets

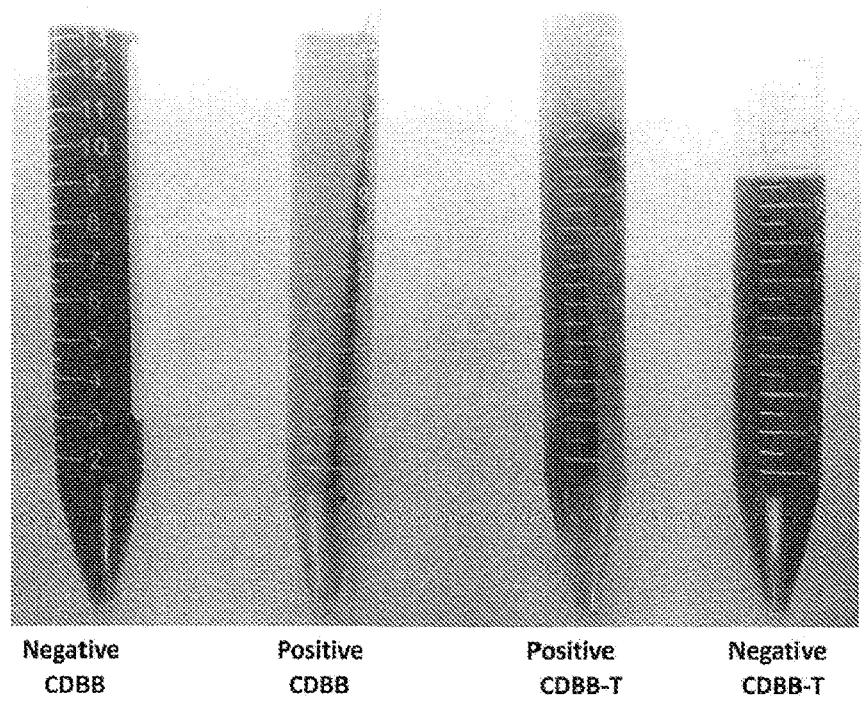
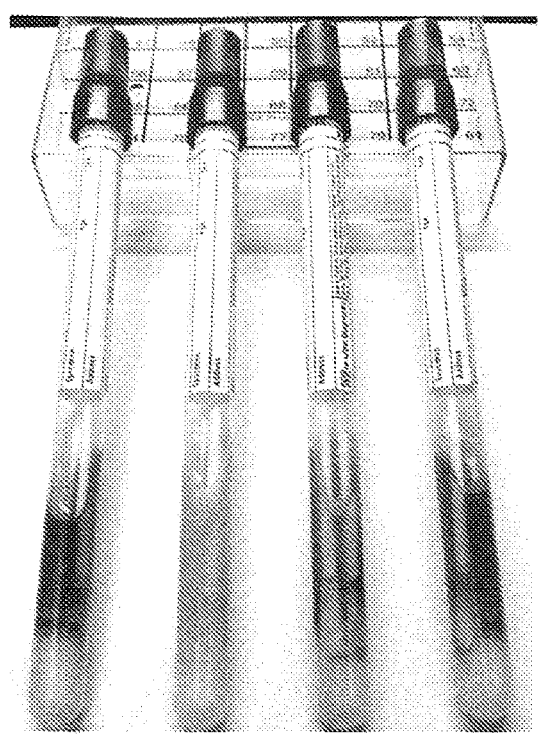
Figs. 3A-B

CLOSTRIDIUM DIFFICILE CULTURE MEDIUM

RELATED APPLICATION

This application claims priority from U.S. Provisional Application No. 62/005,120. filed May 30, 2014, the subject matter of which is incorporated herein by reference in its entirety.

GOVERNMENT FUNDING

This invention was made with government support under Grant No. HS020004 awarded by The National Institutes of Health Agency for Health Care Research and Quality and the Veteran's Affairs Merit Review Award PA-10-089. The United States government has certain rights to the invention.

BACKGROUND

*Clostridium difficile* is an important healthcare-associated pathogen that causes diarrhea and colitis. Environmental contamination is an important source for transmission of *C. difficile* and detection of environmental contamination can be very useful to guide infection control interventions. However, there are currently no easy to use and inexpensive methods for detection of environmental contamination. Current culture-based detection methods are sensitive, but their utility is hindered by the requirement for anaerobic culture conditions and microbiological expertise.

SUMMARY

Embodiments described herein relate to a culture medium for culturing *Clostridium difficile* under aerobic culture conditions. The medium can include a nutrient medium that promotes growth of *Clostridium difficile* and amounts of thioglycolic and L-cystine effective to consume oxygen in the culture medium and facilitate growth of *Clostridium difficile*. A culture medium containing thioglycolic acid and L-cystine provides a sensitive and selective method for culture of *C. difficile* from environmental specimens without the need for anaerobic culture conditions. The media is easy to prepare, and the requirement for microbiological expertise is minimal because positive broth samples based on color change can be confirmed as *C. difficile* by latex agglutation or EIA for glutamate dehydrogenase or as toxigenic *C. difficile* using commercial polymerase chain reaction assays for toxin genes or enzyme immunoassays for toxin.

Other embodiments described herein relate to a method for detecting and/or identifying *Clostridium difficile*. The method includes inoculating a culture medium with a biological sample to be tested. The culture medium includes a nutrient medium that promotes growth of *Clostridium difficile* and amounts of thioglycolic and L-cystine effective to consume oxygen in the culture medium and facilitate growth of *Clostridium difficile*. The inoculated culture medium is then incubated under aerobic conditions. The presence of *Clostridium difficile* is then determined in the incubated culture medium.

Still other embodiments provide kits for diagnosing the presence of *Clostridium difficile* comprising culture media and protocols disclosed herein.

BRIEF DESCRIPTION OF THE DRAWINGS

FIGS. 3(A-B) illustrate images showing positive and negative cultures of *C. difficile* in CDBB and CDBB-TC.

DETAILED DESCRIPTION

Figure 1:
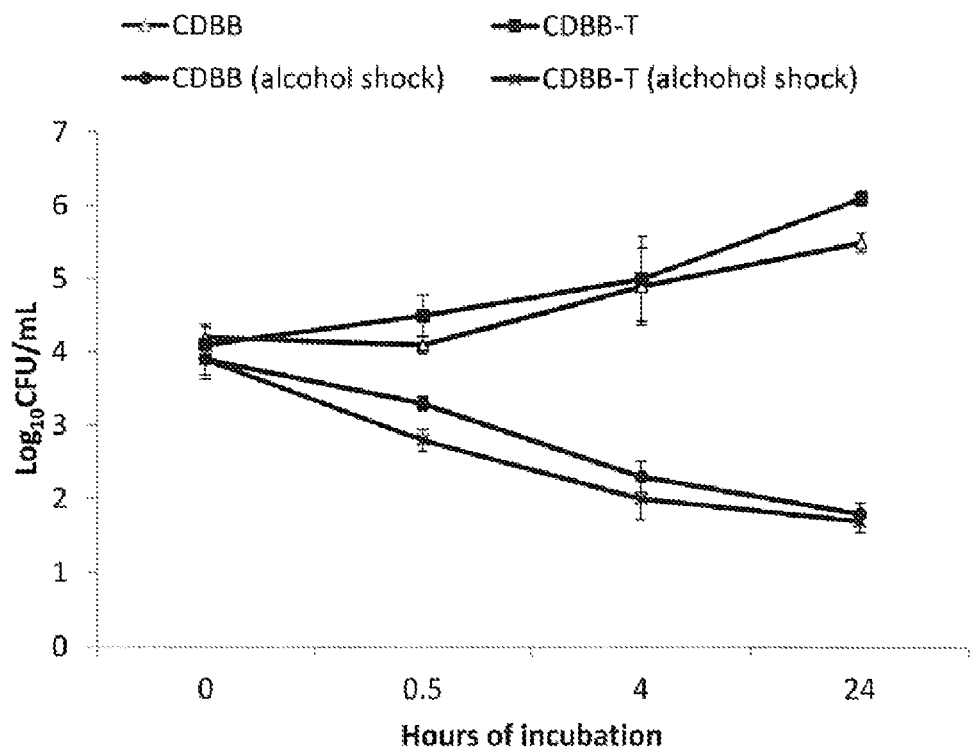
FIG. 1 illustrates plots showing the rate and extent of germination and outgrowth of *Clostridium difficile* in *Clostridium difficile* Brucella broth (CDBB) and *C. difficile* Brucella broth with thioglycolic acid and L-cystine (CDBB-TC).

Embodiments described herein relate to a culture medium that can be used to culture *Clostridium difficile* from a biological sample and to a method for detecting and/or identifying *C. difficile*, which uses such a medium. The culture medium includes amounts of thioglycolic and L-cystine effective to consume oxygen in the culture medium and facilitate growth of *C. difficile*. A culture medium including thioglycolic acid and L-cystine provides a sensitive and selective method for culture of *C. difficile* from environmental specimens without the need for anaerobic culture conditions and thus the *C. difficile* can be cultured under aerobic conditions.

The culture medium is as sensitive as standard anaerobic culture methods for detection of asymptomatic carriers of *C. difficile* based on perirectal culture results. The culture medium can be used to detect asymptomatic carriers of *C. difficile* based upon either perirectal or skin (chest/abdomen) cultures. The fact that there is no need for an anaerobic chamber or significant microbiologic expertise allows the culture medium to be used in most hospitals or long-term care facilities.

In some embodiments, the culture medium includes a nutrient medium that promotes growth of *C. difficile* in addition to the amounts of thioglycolic and L-cystine effective to consume oxygen in the culture medium and facilitate growth of *C. difficile*. The nutrient medium may be solid, semi-solid or liquid. The term "solid medium" is intended to mean, for example, a gelled medium. Agar is the conventional gelling agent in microbiology for culturing microorganisms, but it is possible to use gelatin, agarose or other natural or artificial gelling agents.

In some embodiments, the nutrient can include Brucella broth, which is a general purpose broth for the cultivation of microorganisms. Brucella broth can include, for example, tryptone (10 grams per liter), peptamin (10 grams per liter), glucose (1 gram per liter) yeast extract (2 grams per liter) sodium chloride (5 grams per liter) and sodium bisulphite (0.1 gram per liter).

The thioglycolic and L-cystine are provided in the culture medium as reducing agents to facilitate growth of *C. difficile* and neutralize the dissolved $O_2$ present in the medium. Advantageously, it was found that by including both thioglycolic and L-cystine in the culture medium *C. difficile* can be cultured under aerobic culture condition to provide inexpensive detection and recovery of *C. difficile* from environmental samples. Additionally, it was found that the combination of L-cystine and thioglycolic acid provided greater sensitivity and more consistent recovery of *C. difficile* than either reducing agent alone when included in the culture medium.

In some embodiments, the amount of thioglycolic provided in the culture medium can be about 0.1 g/l to about 10 g/l, about 0.5 g/l to about 5 g/l, or about 0.5 g/l to about 2.5 g/l. In other embodiments, the amount of L-cystine provided in the culture medium can be about 0.1 g/l to about 10 g/l, about 0.5 g/l to about 5 g/l, or about 0.5 g/l to about 2.5 g/l.

The culture medium can include one or more additional elements in combination, such as amino acids, peptones, carbohydrates, nucleotides, minerals, vitamins, etc. The medium may also comprise a colorant. By way of indication, as a colorant, mention may be made of Evans blue, neutral red, sheep blood, horse blood, an opacifier such as titanium oxide, nitroaniline, malachite green, brilliant green, one or more metabolic indicators, one or more metabolic regulators, etc.

The culture medium may also comprise one or more growth activators for *C. difficile* strains. The term growth activator is intended to mean a compound or a group of compounds which stimulates the growth of microorganisms.

The culture medium may also include one or more *C. difficile* spore germination inducers. The term spore germination inducer is intended to mean a compound or a group of compounds which promotes the change from the spore state to the vegetative state of *C. difficile*. In some embodiment the spore inducer provided in the culture medium can be sodium taurocholate. For example, sodium taurocholate can be included in the culture medium at a concentration of about 0.1 g/l to about 10 g/l, about 0.5 g/l to about 5 g/l, or about 0.5 g/l to about 2.5 g/l.

In some embodiments, the culture medium can include one or more selective agents. The term selective agent is intended to mean any compound capable of preventing or slowing down the growth of a microorganism. The concentration of a selective agent provided in the culture medium can be about 5 mg/l to about 5 g/l.

Examples of selective agents can include an antibiotic, such as D-cycloserine, cephalosporins, such as cefoxitin or cefotaxime, colistin, polymyxin, fosfomycin, tobramycin, gentamicin, aztreonam, trimethoprim, quinolones, such as nalidixic acid, an antifungal, such as amphotericin B, fluconazole or itraconazole.

The term "antibiotic" is intended to mean any compound capable of preventing or slowing down the growth of a bacterium. They belong in particular to the cephalosporin, aminoglycoside, polypeptide, sulfamide and quinolone groups. By way of indication, mention may in particular be made of the antibiotics cefotaxime, ceftazidime, cefoxitin, ceftriaxone, cefpodoxime, aztreonam, trimethoprim, tobramycin, moxalactam, fosfomycin, D-cylcoserine, polymyxin and colistin.

The term "antifungal" is intended to mean any compound capable of preventing or slowing down the growth of yeast or of a mold. By way of indication, mention may in particular be made of amphotericin B, fluconazole, itraconazole, voriconazole and cycloheximide.

In some embodiments, the culture medium can have a pH of about 7 to about 8, for example about 7.6 to stimulate the germination of *C. difficile* spores.

In one example, the culture medium can consist essentially of or consist of Brucella broth, vitamin $K_1$ solution, hemin solution, sodium bicarbonate solution, D-mannitol, sodium taurocholate, lysozyme, D-cycloserine, cefoxitin, agar, thioglycolic acid, and L-cystine.

The culture medium can be used in an assay or method for detecting and/or identifying *C. difficile* in a sample. The sample can be, for example, an environmental sample. Environmental samples can be obtained from, for example, surfaces suspected of being contaminated with *C. difficile*, such as, for example, hospital equipment, such as be rails, tables, chairs, physical therapy equipment. The sample can be a biological sample from a specimen of food, biological flood, or biological waste, such as stool. The sample can be a solid or a liquid.

In the method, the collected sample can be inoculated in the culture medium described herein. The inoculated culture medium can then be cultured under aerobic conditions for about 6 hours, 12 hours, 24 hour, 72 hours or more at a temperature, for example, of about 37° C.

The presence of *C. difficile* in the incubated culture medium can determined by, for example, measuring *C. difficile* spore generation in the incubated culture medium, using at least one of a PCR assay for toxin B genes, using an enzyme immunoassay for toxin, using an enzyme immunoassay for glutamate dehydrogenase, or using latex agglutination assay.

Still other embodiments described herein relate to a kit for diagnosing the presence of toxigenic *Clostridium difficile* where the kit comprises any of the culture media disclosed herein. The kit can also include culture swabs, and a culture vessel, such as polystyrene tubes. The kit can further include a confirmatory test, such as a *C. difficile* latex agglutination test, to be used on tubes that shows, for example, a positive color change upon presence of *C. difficile* in a specimen. The kit can also include instructions for carrying out any of the methods disclosed herein.

Example

We developed a low cost selective broth medium containing thioglycolic acid, termed *C. difficile* Brucella broth with thioglycolic acid and L-cystine (CDBB-TC) that is easy to use and sensitive and specific for detection of *C. difficile* from environmental specimens under aerobic culture conditions.

We evaluated the utility of using a commercial PCR assay for toxin B genes, enzyme immunoassay for toxin, enzyme immunoassay for glutamate dehydrogenase, or *C. difficile* latex agglutination assay as confirmatory tests for positive broth specimens. Our goal was to develop an effective assay that would be inexpensive and easy to use.

Methods

*C. difficile* Strains

Two *C. difficile* strains were studied. Strain VA 17 is an epidemic restriction endonuclease analysis (REA) type BI strain and strain VA 11 is an REA J-type strain.

Preparation of Spores

Spores were prepared by growth on Duncan and Strong agar medium. Spores were stored at 4° C. in sterile distilled water until use. Spores were confirmed by phase contrast microscopy and malachite green staining to be >98% free of vegetative cells or cell debris.

Modified Media for Culture of *C. difficile* in Room Air

The base medium that was modified for the purposes of this study was *Clostridium difficile* Brucella broth (CDBB). Under anaerobic conditions, CDBB was previously shown to stimulate germination and outgrowth of *C. difficile* spores at a rate comparable to cycloserine-cefoxitin-fructose broth and an agar formulation was as sensitive and selective as cycloserine-cefoxitin-fructose agar for recovery of *C. difficile* from stool specimens. The modified broth culture medium devised for growth of *C. difficile* in room air was termed *C. difficile* Brucella Broth with thioglycolic acid and L-cystine (CDBB-TC). Table 1 shows ingredients for CDBB-TC. For CDBB-TC, brucella broth powder (Sigma-Aldrich, St. Louis, Mo.), vitamin K1, hemin, sodium bicarbonate, agar, mannitol, neutral red solution prepared in absolute ethanol, thioglycolic acid (mercaptoacetic acid), L-cystine, and agar were prepared in 1,000 ml of distilled water as described previously. Mannitol and neutral red were added in order to distinguish *C. difficile* colonies by the typical yellow color change associated with fermentation of mannitol. The media was adjusted to pH 7.6, autoclaved at 121° C. for 15 min, and cooled to 50° C. in a water bath. Sterile solutions of cycloserine, cefoxitin, sodium taurocholate, and lysozyme were prepared in distilled water and added to the cooled base broth. The medium was either used within 2 weeks of preparation or boiled prior to use.

TABLE 1

Formulation of *Clostridium difficile brucella* broth with thioglycolic acid (CDBB-TC)

| Ingredients | Quantity/L |
|---|---|
| *Brucella* Broth | 28.0 |
| Vitamin $K_1$ solution (1 mg/mL) | 1.0 mL |
| Hemin solution (5 mg/mL) | 1.0 mL |
| Sodium bicarbonate solution (20 mg/mL) | 5.0 mL |
| D-Mannitol | 6.0 g |
| Neutral red solution (1%) | 5.0 mL |
| Sodium taurocholate | 0.5 g |
| Lysozyme | 5.0 mg |
| D-cycloserine | 500.0 mg |
| Cefoxitin | 16.0 mg |
| Agar | 1.0 g |
| Thioglycolic acid (mercaptoacetic acid) | 1.0 g |
| L-cystine | 1.0 g |

Preliminary experiments demonstrated that the combination of L-cystine and thioglycolic acid provided greater sensitivity and more consistent recovery of *C. difficile* than either reducing agent alone (data not shown). Previously, we did not find that the addition of lysozyme to COBA significantly increased recovery of *C. difficile* spores. However, lysozyme was maintained because some studies have suggested that it may stimulate spore germination and increase the recovery of environmental *C. difficile* spores.

For environmental cultures, 10 mL of CDBB-TC was added to 15 mL conical polystyrene centrifuge tubes (Thermo Fisher Scientific, Rochester, N.Y.). BD BBL CultureSwabs (Becton Dickinson, Cockeysville, Md.) swabs were applied to surfaces and swab heads were broken off and submersed in the media. The tubes were capped and placed inside an incubator at 37° C. in room air for 72 hours. An alternative approach was also evaluated in which 3 or 5 mL of CDBB-TC was pipetted into the culture swab holder (i.e., the plastic tube containing the swab) at the time the collected swab was being processed; the swab was then inserted back into its holder and incubated.

Germination and Outgrowth of *C. difficile* in CDBB Versus CDBB-TC

To compare the rate and extent of *C. difficile* spore germination in COBB-TC versus CDBB, spores of the two test strains ($10^4$ CFU/mL) were added to CDBB (anaerobic chamber) or CDBB-TC (room air incubator) and incubated for 24 hours at 37° C. Aliquots were removed at 0.5, 4, 6, and 24 hours diluted 1:1 in either phosphate buffered saline (PBS) or absolute ethanol, then serially diluted in PBS and plated on pre-reduced CDBA plates inside a Whitley Workstation MG1000 anaerobic chamber (Microbiology International, Frederick, Mo.) to enumerate CFU. The ethanol-shock method provides a measurement of the spore concentration, whereas the samples diluted in PBS provide a measurement of the total *C. difficile* count (i.e., spores and vegetative cells). All experiments were performed in triplicate.

Comparison of Sensitivity and Selectivity of CDBB-TC and COBB in the Laboratory

In the laboratory, we compared the sensitivity of CDBB-TC under aerobic conditions with that of CDBB under anaerobic conditions inside the anaerobic chamber. Ten µl aliquots of serial dilutions of spores of the two test strains in sterile water were applied to polyester swabs (Fisher Scientific, Rochester, N.Y.) that were inoculated into 15 mL of CDBB-TC or pre-reduced CDBB in 20 mL plastic conical tubes (Fisher Scientific, Rochester, N.Y.). Agitation was kept to a minimum. After 72 hours of incubation at 37° C., specimens with a color change from red to yellow were plated onto pre-reduced CDBA plates inside the anaerobic chamber to determine if *C difficile* was present. For a subset of positive CDBB-TC specimens, confirmatory testing was performed on an aliquot from the bottom of the CDBB-TC tube with color change to yellow using a commercial PCR assay (Xpert *C. difficile*, Cepheid, Sunnyvale, Calif.), enzyme immunoassays (EIA) for glutamate dehydrogenase and toxins A and B, and *C. difficile* latex agglutination (Microgen Bioproducts, Camberley, United Kingdom). The experiments were repeated 9 times.

To assess selectivity, Clostridium sporogenes (ATCC 11437) and *Clostridium perfringens* (ATCC 131124) and *Bacillus subtilis* (ATCC) spores and facultative organisms including *Enterococcus faecium* (strain C68), methicillin-resistant *Staphylococcus aureus* (clinical isolate), *Staphylococcus warnerii* (ATCC 14990), and *Candida glabrata* (ATCC 90030) were incubated in CDBB, CDBB-TC (incubated in room air incubator), and CDBB-TC (incubated inside the anaerobic chamber) at 37° C. for 72 hours. Samples with a color change from red to yellow were plated onto blood plates to assess growth of the organisms.

Comparison of Sensitivity and Selectivity of CDBB-TC and CDBB for Detection of Environmental Contamination on Hospital Wards We evaluated the sensitivity and selectivity of CDBB-TC versus CDBB for detection of environmental contamination. BD BBL CultureSwabs (Becton Dickinson) with 2 swab prongs were applied to surfaces in CD 1 patient rooms and on portable equipment. The swabs were pre-moistened in Dey-Engley Neutralizing broth (Remel Products, Lenexa, Kans.) and applied to a 5×10 cm area of the surfaces. One prong was transferred to the anaerobic chamber and inoculated into pre-reduced CDBB inside the anaerobic chamber and the other was inoculated into CDBB-TC in room air and placed in an incubator in room air. The cultures were incubated at 37° C. for 72 hours. All specimens with a color change from red to yellow were plated onto pre-reduced CDBA inside the anaerobic chamber and incubated for 72 hours. Yellow colonies with the typical appearance were streaked for isolation onto blood plates and were confirmed to be *C. difficile* on the basis of the typical odor and appearance of colonies and by a positive reaction using *C. difficile* latex agglutination. For a subset of specimens with yellow color change, confirmatory testing was also performed using the commercial PCR assay and EIA for glutamate dehydrogenase and toxins A and B as described previously.

To evaluate false-positive cultures (i.e., cultures that turned yellow but did not grow *C. difficile* when the culture medium was plated on CDBA), colonies from CDBA that were not consistent with *C. difficile* based on color and morphology were transferred to blood plates and identified by using the RapID ANA II system (Remel Products, Lenexa, Kans.) for obligate anaerobes or the Vitek 2 system (bioMerieux, Durham, N.C.) for facultative organisms.

Organisms that were identified were then inoculated into CDBB and CDBB-TC to re-assess growth and color change.

Effect of Thioglycolic Acid on Stimulation of Germination of *C. difficile* Spores To investigate potential explanations for increased recovery of environmental *C. difficile* by CDBB-TC compared with CDBB, we tested the hypothesis that thioglycolic acid stimulates germination of *C. difficile* spores, with the degree of germination varying based on pH. Spore germination was compared in sterile water (control) versus sterile water supplemented with thioglycolic acid 1 mg/mL alone or in combination with lysozyme 1 mg/mL and at pH 5 versus 7.6. To assess germination, spores ($10^6$ colony-forming units [CFU]) were added to 1 mL of each solution and incubated in room air at 22° C. for 1 hour and then 100 μL aliquots were subjected to heat shock at 80° C. for 5 minutes in a water bath (activated spores are killed at 80° C., whereas non-germinated spores are not). After heat shock, samples were serially diluted and plated onto pre-reduced *C. difficile* Brucella agar (CDBA) in the anaerobic chamber at 37° C. for 72 hours and counts were calculated. All experiments were repeated in triplicate.

Data Analysis

Fisher's exact test was used to compare proportions of cultures positive for *C. difficile* and non-*C. difficile* breakthrough growth.

Results

Germination and Outgrowth of *C. difficile* in CDBB Versus CDDD-TC

As shown in FIG. 1, the rate and extent of *C. difficile* spore germination and outgrowth were similar in CDBB-TC and CDBB (FIG. 1). Approximately 90% of the spores (1 log) germinated within 30 minutes based upon susceptibility to alcohol.

Comparison of Sensitivity and Selectivity of COBB-TC and COBB in the Laboratory

Figure 2:
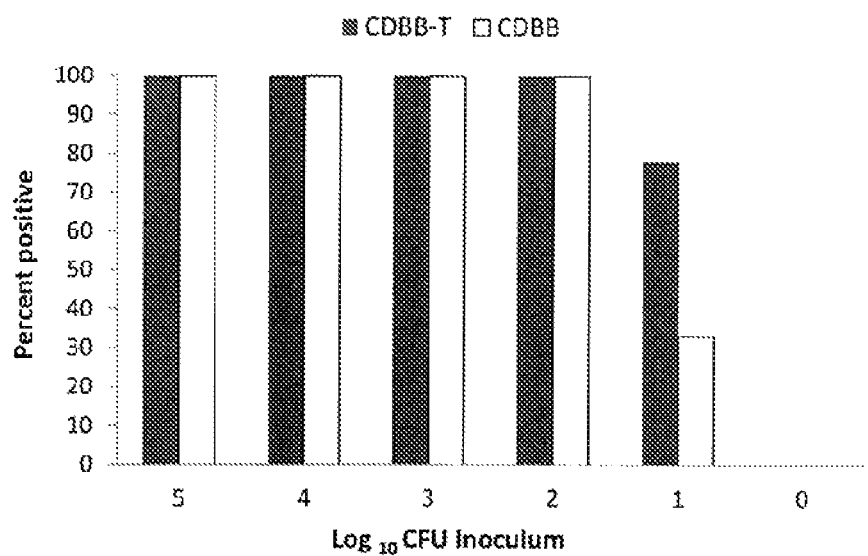
FIG. 2 illustrates a graph comparing the sensitivity and selectivity of CDBB-TC and CDBB for recovery of *C. difficile* spores from inoculated spores.

CDBB-TC was equivalent to COBB for recovery of *C. difficile* spores from inoculated swabs (FIG. 2). CDBB-TC and CDBB consistently yielded positive results from swabs inoculated with ≥2 $\log_{10}$ CFU of spores. Positive results were obtained from a subset of swabs inoculated with 1 $\log_{10}$ CFU of spores; 3 of 9 (33%) runs were positive for CDBB versus 7 of 9 (78%) for CDBB-TC (P=0.15). Positive cultures for CDBB were yellow in color throughout the media tube, whereas positive CDBB-TC cultures were yellow at the bottom of the tube (FIG. 3A). For positive CDBB-TC tubes, aliquots of broth from the bottom of the tube were consistently positive by PCR for toxin B genes, EIA for glutamate dehydrogenase and toxins A and B, and *C. difficile* latex agglutination.

None of the organisms used to assess selectivity grew in CDBB-TC incubated in room air. However, the *C. sporogenes* and *C. perfringens* strains grew in CDBB and in CDBB-TC that was incubated inside the anaerobic chamber.

The alternative approach in which 3 or 5 mL of CDBB-TC was pi petted into the CultureSwab holder was also effective in lab testing (FIG. 3B). However, growth tended to be slower for these specimens, requiring 4 to 5 days for development of the full yellow color change.

Figure 4:
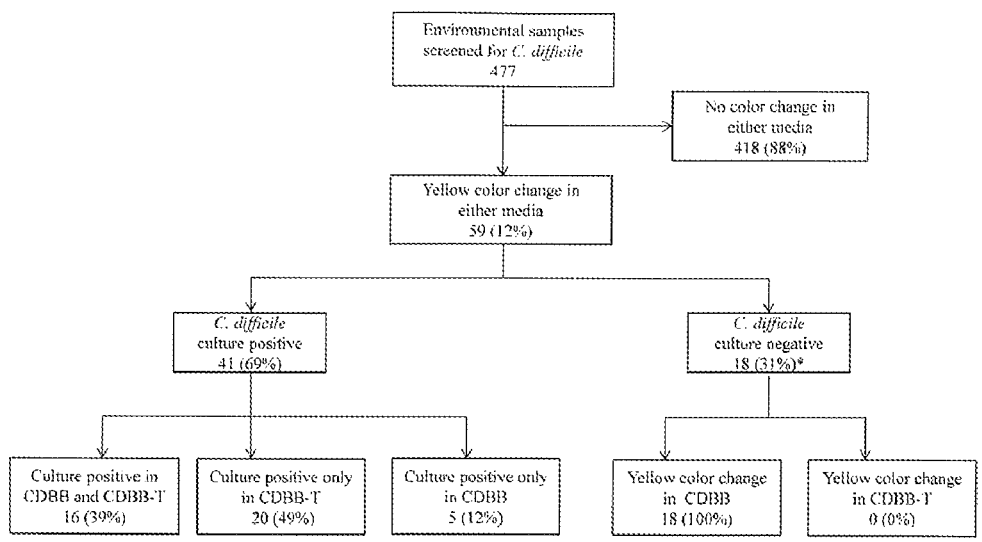
FIG. 4 illustrates a flow diagram comparing the sensitivity of cultures of *C. difficile* in CDBB and CDBB-TC.

Comparison of Sensitivity and Selectivity of CDBB-TC and COBB for Detection of Environmental Contamination on Hospital Wards Environmental swabs were collected from 477 total surfaces (345 from surfaces in CDI patient rooms and 132 from portable equipment). As shown in FIG. 4, 41 (9%) of the cultures were positive by CDBB-TC and/or CDBB based on a subculture onto CDBA yielding *C. difficile*: 16 of the cultures were positive from both culture media, 20 were positive only from CDBB-TC, and 5 were positive only from CDBB.

If any positive culture with confirmed *C. difficile* was consider the gold standard, CDBB-TC was significantly more sensitive than CDBB (36/41, 88% versus 21/41,51%; P=0.006). For culture positive specimens, *C. difficile* latex agglutination was consistently positive from an aliquot from the bottom of the CDBB-TC tube. For 18 culture-positive specimens from CDBB-TC, confirmatory testing of aliquots from the bottom of the CDBB-TC tubes was also positive by PCR for toxin B genes and EIA for glutamate dehydrogenase.

For the 477 total environmental cultures, CDBB-TC was significantly more selective than CDBB (0/477,0% versus 18/477, 4%; P=0001) based upon false-positive yellow color development of the media without recovery of *C. difficile*. The 18 false-positive cultures for CDBB were attributable to growth of non-*C. difficile* anaerobic organisms that did not grow in CDBB-TC in room air. Fourteen colonies from false-positive cultures that were not consistent with *C. difficile* were identified as Fusobacterium spp. (N=6), *Clostridium perfringens* (N=3), *Clostridium septicum* (N=2), *Clostridium tertium* (N=1), *Streptococcus constellatus* (N=1), and *Bacteroides fragilis* (N=1). Inoculation of these organisms into CDBB or CDBB-TC inside the anaerobic chamber resulted in yellow color and growth, whereas inoculation into CDBB-TC with incubation in room air did not.

Figure 5:
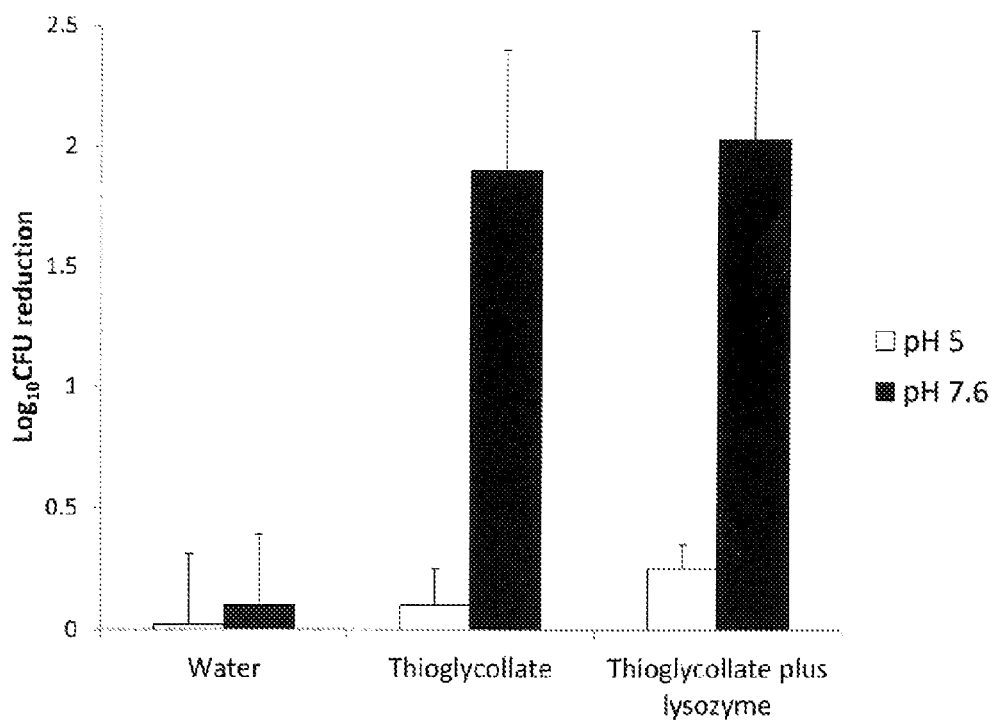
FIG. 5 illustrates the effect of thioglycolic acid on stimulation of germination of *C. difficile* spores.

Effect of Thioglycolic Acid on Stimulation of Germination of *C. difficile* Spores As shown in FIG. 5, minimal germination (based upon reduction in spores at 80° C.) of *C. difficile* spores occurred in sterile water or in thioglycolic acid 1 mg/mL alone or in combination with lysozyme 1 mg/mL at pH 5; however, at pH 7.6 a 2 log reduction in spores occurred at 80° C. in thioglycolic acid 1 mg/mL with no enhancement by lysozyme.

Our findings demonstrate that a broth medium containing thioglycolic acid and L-cystine provides a sensitive and selective method for culture of *C. difficile* from environmental specimens without the need for anaerobic culture conditions. The media is easy to prepare. Moreover, the requirement for microbiological expertise is minimal because positive broth samples based on color change can be confirmed as *C. difficile* by latex agglutination or EIA for glutamate dehydrogenase or as toxigenic *C. difficile* using commercial polymerase chain reaction assays for toxin genes or enzyme immunoassays for toxin.

The fact that *C. difficile* was recovered more frequently from environmental swabs inoculated into CDBB-TC than in CDBB was unexpected. It has been reported that lysozyme enhanced recovery of *C. difficile* from environmental samples, but pre-exposure to alkaline thioglycollate did not further improve recovery. Our results suggest that one potential explanation for the increased recovery of environmental spores could be stimulation of germination by thioglycolic acid. At pH 7.6, but not pH 5, thioglycolic acid stimulated germination of *C. difficile* spores based upon susceptibility of spores to killing by heating to 80° C. The fact that greater stimulation of germination occurred at pH 7.6 could be due to a change to the salt form (sodium thioglycolate) at elevated pH. It is possible that thioglycolic acid/sodium thioglycolate stimulates germination of a fraction of spores from the environment that exists in a super-dominant state. Alternatively, some studies have suggested that thioglycolic acid exposure may sensitize spores to the activity of lysozyme, presumably by rupturing disulphide bonds and increasing penetration of lysozyme to the site of action.

The finding that CDBB-TC was more selective than CDBB was also unexpected. Selectivity of the media is an advantage because extra work and expense is required to evaluate false-positive cultures that turn yellow due to growth of organisms other than *C. difficile*. A variety of anaerobic organisms grew in CDBB and caused a color change to yellow; these organisms did not grow in CDBB-TC incubated in room air, but did grow in COBB-TC incubated inside the anaerobic chamber. We postulate that some of these organisms may be more fastidious than *C. difficile* in their requirement for obligate anaerobic conditions (i.e., CDBB-TC incubated in room air may be sufficiently anaerobic to grow *C. difficile* but not the other *Clostridium* spp. that only grew in anaerobic conditions).

While this invention has been particularly shown and described with references to preferred embodiments thereof, it will be understood by those skilled in the art that various changes in form and details may be made therein without departing from the scope of the invention encompassed by the appended claims. All patents, publications and references cited in the foregoing specification are herein incorporated by reference in their entirety.

Having described the invention, we claim:

1. A method for detecting and/or identifying *Clostridium difficile*, comprising:

inoculating a culture medium with a sample to be tested, the culture medium consisting essentially of brucella broth, vitamin $K_1$ solution, hemin solution, sodium bicarbonate solution, D-mannitol, sodium taurocholate, lysozyme, D-cycloserine, cefoxitin, agar, thioglycolic acid, and L-cystine, wherein the amounts of thioglycolic acid and L-cystine in the culture medium are effective to consume oxygen in the culture medium and facilitate growth of *Clostridium difficile*;

incubating the inoculated culture medium under aerobic conditions; and determining the presence of *Clostridium difficile* in the incubated culture medium, wherein the presence of *Clostridium difficile* is determined by measuring *Clostridium difficile* spore generation in the incubated culture medium.

* * * * *